US008128707B2

(12) United States Patent
Atala

(10) Patent No.: US 8,128,707 B2
(45) Date of Patent: Mar. 6, 2012

(54) BLADDER RECONSTRUCTION

(75) Inventor: Anthony Atala, Winston Salem, NC (US)

(73) Assignee: Children's Medical Center Corporation, Boston, MA (US)

( * ) Notice: Subject to any disclaimer, the term of this patent is extended or adjusted under 35 U.S.C. 154(b) by 240 days.

(21) Appl. No.: 12/468,983

(22) Filed: May 20, 2009

(65) Prior Publication Data

US 2009/0263464 A1 Oct. 22, 2009

Related U.S. Application Data

(63) Continuation of application No. 10/394,640, filed on Mar. 21, 2003, now Pat. No. 7,569,076, which is a continuation of application No. 09/600,455, filed as application No. PCT/US98/22962 on Oct. 30, 1998, now Pat. No. 6,576,019.

(60) Provisional application No. 60/063,790, filed on Oct. 31, 1997.

(51) Int. Cl.
*A61F 2/04* (2006.01)

(52) U.S. Cl. ............... 623/23.65; 623/23.64; 623/23.72; 623/23.75

(58) Field of Classification Search ............... 623/14.13, 623/23.64, 23.65, 23.67, 23.72, 23.75
See application file for complete search history.

(56) References Cited

U.S. PATENT DOCUMENTS

| 3,463,158 A | 8/1969 | Schmitt et al. |
| 4,182,339 A | 1/1980 | Hardy, Jr. |
| 4,458,678 A | 7/1984 | Yannas et al. |
| 4,520,821 A | 6/1985 | Schmidt et al. |
| 4,594,407 A | 6/1986 | Nyilas |
| 4,769,037 A | 9/1988 | Midcalf |
| 4,963,489 A | 10/1990 | Naughton et al. |
| 4,996,154 A | 2/1991 | Gabriels, Jr. |
| 5,032,508 A | 7/1991 | Naughton et al. |
| 5,085,629 A | 2/1992 | Goldberg |
| 5,092,886 A | 3/1992 | Dobos-Hardy |
| 5,160,490 A | 11/1992 | Naughton et al. |
| 5,224,953 A | 7/1993 | Morgentaler |
| 5,261,898 A | 11/1993 | Polin |

(Continued)

FOREIGN PATENT DOCUMENTS

DE 1999/00152 1/1999

(Continued)

OTHER PUBLICATIONS

Atala, A. et al., J. Urol., 148:658-662 (1992). "Formation of Urethlial Structures in Vivo from Dissociated Cells Attached to Biodegradable Polymer Scaffolds in Vitro."

(Continued)

*Primary Examiner* — Thomas J Sweet
*Assistant Examiner* — Rebecca Straszheim
(74) *Attorney, Agent, or Firm* — Nixon Peabody LLP

(57) ABSTRACT

The invention is directed to methods and devices for the reconstruction, repair, augmentation or replacement of laminarily organized luminal organs or tissue structures in a patient in need of such treatment. The device comprises a biocompatible synthetic or natural polymeric matrix shaped to conform to at least a part of the luminal organ or tissue structure with a first cell population on or in a first area and a second cell population such as a smooth muscle cell population in a second area of the polymeric matrix. The method involves grafting the device to an area in a patient in need of treatment. The polymeric matrix comprises a biocompatible and biodegradable material.

18 Claims, 7 Drawing Sheets

U.S. PATENT DOCUMENTS

| | | | |
|---|---|---|---|
| 5,376,376 A | 12/1994 | Li | |
| 5,429,674 A | 7/1995 | Lamers | |
| 5,429,938 A | 7/1995 | Humes | |
| 5,433,996 A | 7/1995 | Kranzler | |
| 5,443,950 A | 8/1995 | Naughton et al. | |
| 5,480,436 A | 1/1996 | Bakker | |
| 5,514,378 A | 5/1996 | Mikos et al. | |
| 5,516,680 A | 5/1996 | Naughton et al. | |
| 5,545,131 A | 8/1996 | Davankov | |
| 5,549,674 A | 8/1996 | Humes et al. | |
| 5,567,612 A | 10/1996 | Vacanti et al. | |
| 5,613,982 A | 3/1997 | Goldstein | |
| 5,654,273 A | 8/1997 | Gallo et al. | |
| 5,686,289 A | 11/1997 | Humes | |
| 5,709,854 A | 1/1998 | Griffith-Cima | |
| 5,716,404 A | 2/1998 | Vacanti et al. | |
| 5,750,329 A | 5/1998 | Quinn | |
| 5,759,830 A | 6/1998 | Vacanti | |
| 5,762,966 A | 6/1998 | Knapp, Jr. | |
| 5,766,618 A | 6/1998 | Laurencin | |
| 5,770,193 A | 6/1998 | Vacanti | |
| 5,770,417 A | 6/1998 | Vacanti | |
| 5,800,537 A | 9/1998 | Bell | |
| 5,851,833 A | 12/1998 | Atala | |
| 5,855,610 A | 1/1999 | Vacanti | |
| 5,858,721 A | 1/1999 | Naughton | |
| 5,863,531 A | 1/1999 | Naughton | |
| 5,916,265 A | 6/1999 | Hu | |
| 5,947,893 A | 9/1999 | Agrawal et al. | |
| 5,957,972 A | 9/1999 | Williams | |
| 5,962,325 A | 10/1999 | Naughton | |
| 5,967,972 A | 10/1999 | Santilli | |
| 6,018,024 A | 1/2000 | Seubert | |
| 6,140,039 A | 10/2000 | Naughton | |
| 6,171,344 B1 | 1/2001 | Atala | |
| 6,376,244 B1 | 4/2002 | Atala | |
| 6,428,802 B1 | 8/2002 | Atala | |
| 6,576,019 B1 | 6/2003 | Atala | |
| 2002/0150604 A1 | 10/2002 | Yi | |
| 2007/0276507 A1* | 11/2007 | Bertram et al. | 623/23.65 |

FOREIGN PATENT DOCUMENTS

| | | |
|---|---|---|
| DE | 19919625 | 11/2000 |
| EP | 0194192 | 11/1989 |
| GB | 20/11274 | 7/1979 |
| JP | 01/17572 | 3/2001 |
| SU | 1034717 | 8/1983 |
| WO | 88/03785 | 6/1988 |
| WO | 89/01967 | 3/1989 |
| WO | 90/02796 | 3/1990 |
| WO | 90/12604 | 11/1990 |
| WO | 92/15259 | 9/1992 |
| WO | 93/07913 | 4/1993 |
| WO | 95/11048 | 4/1995 |
| WO | 95/24873 | 9/1995 |
| WO | 96/08213 | 3/1996 |
| WO | 96/09372 | 3/1996 |
| WO | 96/31232 | 10/1996 |
| WO | 96/40175 | 12/1996 |
| WO | 98/06445 | 2/1998 |
| WO | 98/09582 | 3/1998 |
| WO | 98/46165 | 10/1998 |
| WO | 99/22677 | 5/1999 |
| WO | 99/22781 | 5/1999 |
| WO | 00/67672 | 11/2000 |
| WO | 01/49827 | 7/2001 |

OTHER PUBLICATIONS

Atala, A. et al, J. Urol., 150:608-612 (1993). "Implantation in Vivo and Retrieval of Artificial Structures Consisting of Rabbit and Human Urothelium and Human Bladder Muscle."

Cilentro, B. et al., J. Urol., 152:665-670 (1994). "Phenotypic and Cytogenetic Characterization of Human Bladder Urothelia Expanded in Vitro."

Kirker-Head, C., Vet. Surg., 24:408-419 (1995). "Recombinant Bone Morphogenetic Proteins: Novel Substances for Enhancing Bone Healing."

Laurencin, C., J. Biomed. Mater. Res., 30:133-138 (1996). "A Highly Porous 3-Dimensional Polyphosphazene Polymer Matrix for Skeletal Tissue Regeneration."

Zdrahala, R., J. Biomater. Appl., 10:309-329 (1996). "Small Caliber Vascular Grafts. Part I: State of the Art."

Alberti C et al. 2004. "What's in the pipeline about bladder reconstructive surgery?" Int J Artif Organs 27:737-743.

Aldskogius H. et al. 2002. "Strategies for repair of the deafferented spinal cord." Brain Res Rev 40:301-308.

Ashkar, S. et al., "Regulation of Gluconeogenesis in Swine Kidney Proximal Tubule Cells," Molecular and Cellular Biochemistry, 87:105-118 (1989).

Atala, A. et al. "Injectable Alginate Seeded with Chondrocytes as Potential Treatment for Vesicoureteral Reflux," The Journal of Urology, vol. 150, 745-7 (Aug. 1993).

Atala A. "Tissue engineering in urologic surgery" In Technologic Advances in Urology. Urologic Clins of North America, 25(1):39-50, 1998.

Atala A. "Tissue Engineering for the replacement organ function in the genitourinary system." Am J Transplant 4 Suppl 6:58-73, 2004.

Ben-Ze'ev, A. et al., "Cell-cell and Cell-matrix Interactions Differentially Regulate the Expression of Hepatic and Cytoskeletal Genes in Primary Cultures of Rat Hepatocytes," PNAS, vol. 85, 2161-5 (Apr. 1988).

Bissell, D. et al., "Interactions of Rat Hepatocytes with Type IV Collagen, Fibronectin and Laminin Matrices. Distinct Matrix-controlled Modes of Attachment and Spreading," European Journal of Cell Biology, vol. 40, 72-8 (1986).

Boogard, P.J. et al., "Renal Proximal Tubular Cells in Suspension or in Primary Culture as In Vitro Models to Study Nephrotoxicity," (ABST) Chem. Biol. Interact, 76(3):251-291 (1990).

Burke, J., "The Effects of the Configuration of an Artificial Extracellular Matrix on the Development of a Functional Dermis," The Role of Extracellular Matrix in Development, Alan R. Liss, Inc., eds (NY), 351-55 (1984).

Castro RF et al. 2002. "Failure of bone marrow cells to transdifferentiate into neural cells in vitro." Science 297:1299.

Cilento, B. et al., "Phenotypic and Cytogenetic Characterization of Human Bladder Urothelia Expanded in Vitro" J. Urol., vol. 152: 665-670 (Aug. 1994).

Courjault-Gautier, F. et al., "Consecutive use of Hormonally Defined Serum-free Media to Establish Highly Differentiated Human Renal Proximal Tubule Cells in Primary Culture,"(ABST) J. Am. Soc. Nephrol., 5(11):1949-1963 (May 1995).

Culliton, B., "Gore Tex Organoids and Genetic Drugs," Science, vol. 246, 747-9 (Nov. 10, 1989).

Daley GQ et al. 2003. "Realistic prospects for stem cell therapeutics." Hematol 2003:398-418.

Davis, G. et al., "Human Amnion Membrane Serves as a Substratum for Growing Axons in Vitro and in Vivo" Science, vol. 236, 1106-9 (May 29, 1987).

Ebata, H. et al., "Liver Regeneration Utilizing Isolated Hepatocytes Transplanted into the Rat Spleen," Surg Forum, vol. 29, 338-40 (1978).

Fontaine, M. et al., "Transplantation of Genetically Altered Hepatocytes Using Cell-Polymer Constructs," Transplantation Proceedings, vol. 25, No. 1, 1002-4 (Feb. 1993).

Fournier, N. et al., "Biological Molecule-impregnated Polyester: An In Vivo Angiogenesis Study," (ABST) Biomaterials, 17(17):1659-1665 (1996).

Genestie, I. et al., "Polarity and Transport Properties of Rabbit Kidney Proximal Tubule Cells on Collagen IV-coated Porous Membranes," (ABST) Am. J. Physiol.,269(1):pt, 2, f22-30 (Jul. 1995).

Gilbert, J. et al., "Cell Transplantation of Genetically Altered Cells on Biodegradable Polymer Scaffolds in Syngeneic Rats," Transplantation, vol. 56, No. 2, 423-7 (Aug. 1993).

Henry, E.W. et al., "Nerve Regeneration Through Biodegradable Polyester Tubes," Experimental Neurology, vol. 90, 652-76 (1985).

Humes, H.D. et al., "Effects of Transforming Growth Factor-beta, Transforming Growth Factor-alpha, and Other Growth Factors on Renal Proximal Tubule Cells," Laboratory Investigation, 64(4):538-545 (1991).

Humes, H.D. et al., "Tubulogenesis From Isolated Single Cells of Adult Mammalian Kidney-Clonal Analysis With a Recombinant Retrovirus," (ABST) Am. J. of Physiology-Renal Fluid and Electrolyte Physiology, 40(1):f42-49 (Jul. 1996).

Humes, H.D. et al., "Replacement of Renal Function in Uremic Animals with a Tissue-Engineered Kidney," Nature Biotechnology, vol. 17, 451-5 (May 1999).

Ingber, D. et al., "Endothelial Growth Factors and Extracellular Matrix Regulate DNA Synthesis Through Modulation of Cell and Nuclear Expansion," In Vitro Cellular * Developmental Biology, vol. 23, No. 5, 387-94 (May 1987).

International Search Report, PCT/US00/33891, Issued Mar. 26, 2001.

Jauregui, H.O. et al., "Attachment and Long Term Survival of Adult Rat Hepatocytes in Primary Monolayer Cultures: Comparison of Different Substrata and Tissue Culture Media Formulations," In Vitro Cellular & Developmental Biology, vol. 22, No. 1, 13-22 (Jan. 1986).

Kirker Head, C., "Recombinant Bone Morphogenetic Proteins: Novel Substances for Enhancing Bone Healing," Vet. Surg., vol. 24:408-419 (1995).

Kirschstein, R. et al., 2001. "Can stem cells repair a damage heart? In Stem cells: scientific progress and future research directions." pp. 87-92.

Langer, R. and Moses, M., "Biocompatible Controlled Release Polymers for Delivery of Polypeptides and Growth Factors," Journal of Cellular Biochemistry, vol. 45, 340-5 (1991).

Laurencin, C., "A Highly Porous 3 Dimensional Polyphosphazene Polymer Matrix for Skeletal Tissue Regeneration" J. Biomed. Mater. Res., vol. 30: 133-138 (1996).

Mezey E et al. and Castro RF et al. 2003. Comments on "Failure of bone marrow cells to transdifferentiate into neural cells in vitro". Science 299: 1184b.

Michalopoulos, G. and Pitot, H.C., "Primary Culture of Parenchymal Liver Cells on Collagen Membrances," Experimental Cell Research, vol. 94, 70-8 (1975).

Mooney, D. and Vacanti, J., "Tissue Engineering Using Cells and Synthetic Polymers," Transplantation Reviews, vol. 7, No. 3, 153-62 (Jul. 1993).

Naughton, B. et al., "Long-term Growth of Rat Bone Marrow Cells in a Three-dimensional Matrix," The Anatomical Record, vol. 218, 97A (1987).

Nikolovski, J. et al., "Design Engineering of a Bioartificial Renal Tubule Cell Therapy Device," Cell Transplantation, vol. 8, 351-64 (1999).

Oberpenning F et al. 1999. "De novo reconstitution of a functional mammalian urinary bladder by tissue engineering." Nat Biotech 17:149-155.

O'Connor, N. et al., "Grafting of Burns with Cultured Epithelium Prepared from Autologous Epidermal Cells," The Lancet, 75-8 (Jan. 10, 1981).

Puelacher, W.C. et al., "Tissue-engineered Growth of Cartilage: The Effect of Varying the Concentration of Chondrocytes Seeded Onto Synthetic Polymer Matrices," Int. J. Oral Maxilofac. Surge., vol. 23, 49-53 (1994).

Reid, L. et al., "Long-term Cultures of Normal Rat Hepatocytes on Liver Biomatrix," Annals New York Academy of Sciences, 70-6 (1980).

Rhine, W. et al., "Polymers for sustained Macromolecule Release: Procedures to Fabricate Reproducible Delivery Systems and Control Release Kinetics," Journal of Pharmaceutical Sciences, vol. 69, No. 3, 265-70 (Mar. 1980).

Rosen, H.B., et al., Bioerodible Polyanhydrides for Controlled Drug Delivery, Biomaterials, vol. 4, 131-3 (Apr. 1983).

Roskams, A.J. et al., Exp. Neurol. 193:267-272 (2005). "Directing stem cells and progenitor cells on the stage of spinal cord injury."

Sawada, N. et al., In Vitro Cellular & Developmental Biology, 23(4) 267-73 (Apr. 1987). "Effects of Extracellular Matrix Components on the Growth and Differentiation of Cultured Rat Hepatocytes."

Seckel, B.R. et al., "Nerve Regeneration Through Synthetic Biodegradable Nerve Guides: Regulation by the Target Organ," Plastic and Reconstructive Surgery, 74(2):173-81 (Aug. 1984).

Shine, H.D. et al., "Cultured Peripheral Nervous System Cells Support Peripheral Nerve Regenerations Through Tubes in the Absence of Distal Nerve Stump," Journal of Neuroscience Research, 14:393-401 (1985).

da Silva, C. et al., "An In Vivo Model to Quantify Motor and Sensory Peripheral Nerve Regeneration Using Bioresorbable Nerve Guide Tubes," Brain Research, 342:307-15 (1985).

Staach, A. et al., 2005, Molecular, cellular and developmental biology of urothelium as a basis of bladder regeneration. Differentiation 73:121-133.

Tachibana, M. et al., "Ureteral Replacement Using Collagen Sponge Tube Grafts," The Journal of Urology, 133:866-9 (May 1985).

Takeda, T. et al., "Hepatocyte Transplantation in Biodegradable Polymer Scaffolds Using the Dalmation Dog Model of Hyperuricosuria," Transplantation Proceedings, vol. 27, No. 1, 635-6 (Feb. 1995).

Taub, M. et al., "Epidermal Growth Factor or Transforming Growth Factor a is Required for Kidney Tubulogenesis in Matrigel Cultures in Serum-Free Medium," Proc. Natl. Acad. Sci., 87:4002-6 (May 1990).

Thompson, J. et al., "Heparin-binding Growth Factor 1 Induces the Formation of Organoid Neovascular Structures in vivo" PNAS, vol. 86, 7928-32 (Oct. 1989).

Thompson, J. et al., "Implantable Bioreactors: Modern Concepts of Gene Therapy," Current Communications in Molecular Biology: Therapeutic Peptides and Proteins, Cold Spring Harbor Laboratory, eds., 143-7 (1989).

Tosh D. et al. 2002. Conversion of pancreatic cells to hepatocytes. Biochem Soc Transact 30; 51-55.

Urry, D. and Pattanaik, A., "Elastic Protein-based Materials in Tissue Reconstruction," Annals New York Academy of Sciences, vol. 831,32-46 (Dec. 31, 1997).

Uyama, S. et al., "Delivery of Whole Liver-equivalent Hepatocyte Mass Using Polymer Devices and Hepatotrophic Stimulation," Transplantation, vol. 55, No. 4, 932-5 (Apr. 1993).

Walton, R. and Brown, R., "Tissue Engineering of Biomaterials for Composite Reconstruction: An Experimental Model," Annals of Plastic Surgery, vol. 30, No. 2, 105-10 (Feb. 1993).

Yoo J. et al., "Cartilage rods as a potential material for penile reconstruction in ambiguous or inadequate genitalia" Pediatrics, 100(s):576, (1997) and Journal of Urology, 160:1164-1168 (1998).

Zdrahala, R., "Small Caliber Vasular Grafts. Part I: State of the Art" J. Biomater. Appl., vol. 10:309-329 (Apr. 1996).

Atala, A., et al., "Formation of urothelial structures in vivo from dissociated cells attaches to biological polymer scaffolds in vivo," J. Urol. Part 1, 148:658 (1992).

Atala, A., et al., "Pediatric urology—future perspectives," In: Clinical Urology, edited by R. J. Krane M.B. Siroky and J. M. Fitzpatrick (Philadelphia: J.B. Lippincott, 1994), pp. 507-524.

Bazeed, et al., "New treatment for urothelial structures," Urology 21:53-57 (1983).

Burke, et al., "Successful use of physiologically acceptable artificial skin in the treatment of an extensive burn injury," Ann. Surg., 194:413 (1981).

Chlapowski, F.J., "Long-term growth and maintenance of stratified rat urothelium in vitro," Cell Tissue Kinet. 22:245-257 (1989).

Cima, et al., "Hepatocyte culture on biodegradable polymeric substrates," Biotechnol. Bioeng. 38.145 (1991).

Craig, P.H., et al., "A biological comparison of polyglactin 910 and polyglycolic acid synthetic absorbable sutures," Surg. 141:1010 (1975).

Freeman, M.R., et al., "Induction and segregation of glial intermediate filament expression in the RT4 family of peripheral nervous system cell lines," Proc. Natl. Acad. Sci. USA 84.5808 (1987).

Green, et al., "Growth of cultured human epidermal cells into multiple epithelia suitable for grafting," Proc. Natl. Acad. Sci. 76:5665 (1979).

Hendren, W.H. et al., "Bladder mucosa graft for construction of the male urethra," J. Pediatr. Surg. 21:189-192 (1986).

Laemmil, U.K., "Cleavage of structural proteins during assembly of the head of bacteriophage T4," Nature (London) 227:680-685 (1970).

Ransley, P.G., et al., "Autologous bladder mucosa graft for urethral substitution," Br. J. Urol. 58:331-333 (1986).

Reznikoff, C.A. et al., "Growth kinetics and differentiation in vitro of normal human uroepithelial cells on collagen gel substrates in defined medium," J. Cell Physiol. 131:285-301 (1987).

Romagnoli, G., et al., "Treatment of posterior hypospadias by the autologous graft of cultures urethral epithelium," New England J. Med. 323:527-530 (1990).

Thuroff, et al., "Cultured Rabbit Vesical Smooth Muscle Cells for Lining of Dissolvable Synthetic Prosthesis," Urology XXI:155-158 (1983).

Tseng, S.C.G., et al., "Correlation of specific kerritans with different types of epithelial differentiation: monoclonal antibody studies," Cell 30:361-372 (1982).

Vacanti, "Beyond Transplantation," Arch. Surg. 123:545 (1988).

Vacanti, et al., "Selective cell transplantation using bioabsorbable artificial polymers as matrices," J. Ped. Surg. 23:3 (1988).

Vacanti, et al., "Synthetic polymers seeded with chondrocytes provide a template for new cartilage formation," J. Plast. Reconstr. Surg. 88:753 (1991).

Atala, A., "Tissue Engineering for Bladder Substitution," World J. Urol., vol. 18:364-370 (2000).

Atala, A. et al., "Renal Cell growth in vivo after attachment to biodegradable polymer scaffolds," J Urology 153:4, 1995.

Pope, IV, J. C. et al., "The ontogeny of canine small intestine submucosa regenerated bladder," J Urology 158:1105-1110, 1997.

Scriven, S. D. et al., "Reconstitution of human urothelium from monolayer cultures," J Urology 158:1147-1153, 1997.

Yoo, J. et al., "Creation of functional kidney structures with excretion of urine-like fluid in vivo," Pediatrics, 98(s):605, 1996.

Yoo, J. J., "A novel gene delivery system using urothelial tissue engineered neo-organs," J Urology 158:1066-1170, 1997.

van der Kwast, T.H. et al., "Establishment and characterization of long terim primary mouse urothelial cell cultures," Urol. Res. 17:289-293 (1989).

Atala et al., The Journal of Urology, 150:608-612 (1993). "Implantation in vivo and retrieval of artificial structures consisting of rabbit and human urothelium and human bladder muscle."

Atala et al., The Journal of Urology, 148:658-662 (1992). "Formation of urothelial structures in vivo from dissociated cells attached to biodegradable polymer scaffolds in vitro."

Atala et al., The Lancet, 367:1241-1246 (2006). "Tissue-engineered autologous bladders for patients needing cystoplasty."

Cilentro, B. et al., J. Urol., 152:665-670 (1994). "Pheotypeic and cytogenetic characterization of human bladder urothelia expanded in vitro."

Kirker-Head, C., Vet. Surg., 24:408-419 (1995). "Recombinant bone morphogenetic proteins: novel substances for enhancing bone healing."

Laurencin, C., J. Biomed. Mater. Res., 30:133-138 (1996). "A highly porous 3-dimensional polyphosphazene polymer matrix for skeletal tissue regeneration."

Oberpenning, et al., Nature Biotechnology, 17:149-155 (1999). "De novo reconstitution of a functional mammalian urinary bladder by tissue engineering."

Pope, J. et al., J. Urol., 158:1105-1110 (1997). "The ontogeny of canine small intestinal submucosa regenerated bladder."

Scriven, S.D. et al., J. Urol., 158:1147-1152 (1997). "Reconstitution of human urothelium from monolayer cultures."

Yoo, J. et al., J. Urol., 158:1166-1170 (1997). "A novel gene delivery system using urothelial tissue engineered neo-organs."

Zdrahala, R., J. Biomater., 10:309-329 (1996). "Small caliber grafts. Part I: State of the art."

CNN.com article, "Doctors grow organs from patents' own cells" Internet Source found at <http://www.cnn.com/2006/HEALTH/conditions/04/03/engineered.organs/index.html> Apr. 4, 2006.

"Dream, the magazine of possibilities" Internet Source found at <http://www.childrenshospital.org/dream/dream_fall06/research_rundown_p.html> printed Nov. 27, 2007.

Grambling, C., Internet Source found at <http://findarticles.com/p/articles/mi_m1200/is_14_169/ai_n16346402/print> Apr. 8, 2006. "Building a bladder: patients for the first time benefit from lab-grown organs."

Laurance, J., Internet Source found at <http://www.truthout.org/cgi-bin/artman/exec/view.cgi/59/18853/printer> Apr. 4, 2006. "Bladder grown in lab hailed as breakthrough for organ transplants."

Reinberg, S., Internet Source found at <http://news.healingwell.com/index.php?p=news1&id=531931> printed Nov. 27, 2007. "Tissue-engineered bladder transplants a success."

* cited by examiner

  
*FIG. 4D*  *FIG. 4E*  *FIG. 4F*

 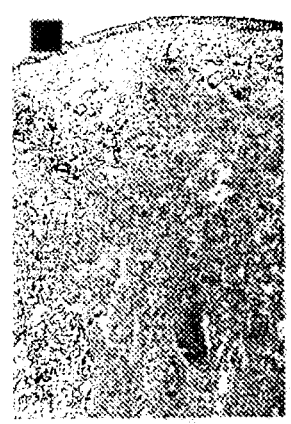 
*FIG. 5A*  *FIG. 5B*  *FIG. 5C*

BLADDER RECONSTRUCTION

CROSS-REFERENCE TO RELATED APPLICATIONS

This application is a continuation of U.S. Application Number 10/394,640 filed on Mar. 21, 2003, which is a continuation of U.S. application Ser. No. 09/600,455 filed on Jul. 17, 2000, now U.S. Pat. No. 6,576,019 issued on Jun. 10, 2003, which is a 35 U.S.C. §371 National Stage of International Application No. PCT/US98/22962 filed on Oct. 30, 1998, which designates the United States, and which claims benefit under 35 U.S.C. §119(e) of U.S. Provisional Application Number 60/063,790 filed on Oct. 31, 1997, the contents of which are incorporated herein by reference.

BACKGROUND

1. Field of the Invention

The invention is directed to methods and materials for tissue reconstruction, repair augmentation and replacement, and particularly to use of such treatments in patients having a defect in urogenital tissues such as the bladder.

2. Description of the Background

The medical community has directed considerable attention and effort to the substitution of defective organs with operationally effective replacements. The replacements have ranged from completely synthetic devices such as artificial hearts to completely natural organs from another mammalian donor. The field of heart transplants has been especially successfully with the use of both synthetic hearts to natural hearts from living donors. Equal success has not been achieved in many other organ fields particularly in the field of bladder reconstruction.

The human urinary bladder is a musculomembranous sac, situated in the anterior part of the pelvic cavity, that serves as a reservoir for urine, which it receives through the ureters and discharges through the urethra. In a human the bladder is found in the pelvis behind the pelvic bone (pubic symphysis) and a drainage tube, called the urethra, that exits to the outside of the body. The bladder, ureters, and urethra are all similarly structured in that they comprise muscular structures lined with a membrane comprising urothelial cells coated with mucus that is impermeable to the normal soluble substances of the urine. The trigone of the bladder, also called the trigonum vesicae, is a smooth triangular portion of the mucous membrane at the base of the bladder. The bladder tissue is elastic and compliant. That is, the bladder changes shape and size according to the amount of urine it contains. A bladder resembles a deflated balloon when empty but becomes somewhat pear-shaped and rises into the abdominal cavity when the amount of urine increases.

The bladder wall has three main layers of tissues: the mucosa, submucosa, and detrusor. The mucosa, comprising urothelial cells, is the innermost layer and is composed of transitional cell epithelium. The submucosa lies immediately beneath the mucosa and its basement membrane. It is composed of blood vessels which supply the mucosa with nutrients and the lymph nodes which aid in the removal of waste products. The detrusor is a layer of smooth muscle cells which expands to store urine and contracts to expel urine.

The bladder is subjected to numerous maladies and injuries which cause deterioration in patients. For example, bladder deterioration may result from infectious diseases, neoplasms and developmental abnormalities. Further, bladder deterioration may also occur as a result of trauma such as, for example, car accidents and sports injury.

Although a large number of bio-materials, including synthetic and naturally-derived polymers, have been employed for tissue reconstruction or augmentation (see, e.g., "Textbook of Tissue Engineering" Eds. Lanza, R., Langer, R., and Chick, W, ACM Press, Colorado (1996) and references cited therein), no material has proven satisfactory for use in bladder reconstruction. For example, synthetic biomaterials such as polyvinyl and gelatin sponges, polytetrafluoroethylene (Teflon) felt, and silastic patches have been relatively unsuccessful, generally due to foreign body reactions (see, e.g., Kudish, H. G., J. Urol. 78:232 (1957); Ashkar, L. and Heller, E., J. Urol. 98:91(1967); Kelami, A. et al., J. Urol. 104:693 (1970)). Other attempts have usually failed due to either mechanical, structural, functional, or biocompatibility problems. Permanent synthetic materials have been associated with mechanical failure and calculus formation.

Naturally-derived materials such as lyophilized dura, deepithelialized bowel segments, and small intestinal submucosa (SIS) have also been proposed for bladder replacement (for a general review, see Mooney, D. et al., "Tissue Engineering: Urogenital System" in "Textbook of Tissue Engineering" Eds. Lanza, R., Langer, R., and Chick, W., ACM Press, Colorado (1996)). However, it has been reported that bladders augmented with dura, peritoneum, placenta and fascia contract over time (Kelami, A. et al., J. Urol. 105:518 (1971)). De-epithelized bowel segments demonstrated an adequate urothelial covering for use in bladder reconstruction, but difficulties remain with either mucosal regrowth, segment fibrosis, or both. It has been shown that de-epithelization of the intestinal segments may lead to mucosal regrowth, whereas removal of the mucosa and submucosa may lead to retraction of the intestinal segment (see, e.g., Atala, A., J. Urol. 156:338 (1996)).

Other problems have been reported with the use of certain gastrointestinal segments for bladder surgery including stone formation, increased mucus production, neoplasia, infection, metabolic disturbances, long term contracture and resorption. These attempts with natural or synthetic materials have shown that bladder tissue, with its specific muscular elastic properties and urothelial permeability functions, cannot be easily replaced.

Due to the multiple complications associated with the use of gastrointestinal segments for bladder reconstruction, investigators have sought alternate solutions. Recent surgical approaches have relied on native urological tissue for reconstruction, including auto-augmentation and ureterocystoplasty. However, auto-augmentation has been associated with disappointing long-term results and ureterocystoplasty is limited to cases in which a dilated ureter is already present. A system of progressive dilation for ureters and bladders has been proposed, however, this has not yet been attempted clinically. Sero-muscular grafts and de-epithelialized bowel segments, either alone or over a native urothelium, have also been attempted. However, graft shrinkage and re-epithelialization of initially de-epithelialized bowel segments has been a recurring problem.

One significant limitation besetting bladder reconstruction is directly related to the availability of donor tissue. The limited availability of bladder tissue prohibits the frequent routine reconstruction of bladder using normal bladder tissue. The bladder tissue that is available, and considered usable, may itself include inherent imperfections and disease. For example, in a patient suffering from bladder cancer, the remaining bladder tissue may be contaminated with metastasis. Accordingly, the patient is predestined to less than perfect bladder function.

SUMMARY OF THE INVENTION

The present invention overcomes the problems and disadvantages associated with current strategies for reconstruction repair of augmentation and replacement of luminal organs and tissue structures.

One embodiment of this invention is directed to a method for the reconstruction, repair, augmentation or replacement of laminarily organized luminal organs or tissue structures in a patient in need of such treatment. The method involves providing a biocompatible synthetic or natural polymeric matrix shaped to conform to at least a part of the luminal organ or tissue structure in need of said treatment, depositing a first cell population on or in a first area of said polymeric matrix, depositing a second cell population of a different cell type than said first cell population in a second area of the polymeric matrix. The second area is substantially separated from the first area. The shaped polymeric matrix cell construct is implanted into the patient at the site in need of treatment to form a laminarily organized luminal organ or tissue structure. Another embodiment of this invention is directed to a device for the reconstruction, repair, augmentation or replacement of laminarily organized luminal organs or tissue structures. The device comprises an implantable, biocompatible, synthetic or natural polymeric matrix with at least two separate surfaces. The polymeric matrix is shaped to conform to a at least a part of the luminal organ or tissue structure in need of said treatment and at least two different cell populations are deposited in substantially separate areas either on or in the polymeric matrix to form a laminarily organized matrix/cell construct.

A further embodiment of this invention is directed to a device for the repair, reconstruction, augmentation or replacement of damaged or missing bladder tissue in a patient in need of such treatment. The device comprises an implantable, biocompatible synthetic or natural polymeric matrix which is shaped to conform to the part of a bladder tissue in need of treatment. Urothelial cells are deposited on and near the inside surface of the matrix, and smooth muscle cells are deposited on and near the outside surface of said matrix. Upon implantation into the patient, the device forms a laminarily organized luminal tissue structure with the compliance of normal bladder tissue.

Other embodiments and advantages of the invention are set forth, in part, in the description which follows and, in part, will be obvious from this description and may be learned from the practice of the invention.

DESCRIPTION OF THE DRAWINGS

The rule of this patent contains at least one drawing executed in color. Copies of this patent with color drawing(s) will be provided by the Patent and Trademark Office upon request and payment of the necessary fee.

FIG. 5: depicts H&E histological results six months after surgery of (A) normal canine bladder; (B) bladder dome of the cell-free polymer reconstructed bladder (group B); (C) the tissue engineered neo-organ (group C).

DESCRIPTION OF THE INVENTION

Figure 1A:
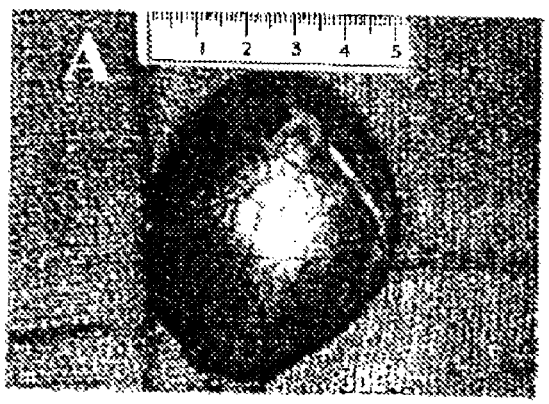
FIG. 1 depicts (A) a native canine bladder prior to trigone-sparing cystectomy; (B) an engineered neo-Organ anastomosed to the trigone; and (C) an implant, decompressed by a transurethral and suprapubic catheter, wrapped with omentum.

The present invention provides methods and devices that facilitate tissue reconstruction. In its broadest form, the methods and devices of the present invention are useful in the reconstruction, repair, augmentation or replacement of organs or tissues structures that comprise multilayer cellular organization and particularly those organs or tissue structures that are luminal in nature. More particularly, the present invention provides methods and devices that facilitate the reconstruction, repair, augmentation or replacement of shaped hollow organs or tissue structures that exhibit a laminar segregation of different cell types and that have a need to retain a general luminal shape. Luminal organs or tissue structures that contain a smooth muscle cell (SMC) layer to impart compliant or contractible properties to the organ or structure are particularly well suited to the methods and devices of the present invention.

In an example of one preferred embodiment of the invention, the luminal organ is the bladder, which has an inner layer of a first cell population that comprises urothelial cells and an outer layer of a second cell population that comprises smooth muscle cells. This organization is also present in other genitourinary organs and tissue structures such as the ureters and urethra. Laminarily organized organs or tissues refer to any organ or tissue made up of, or arranged in laminae including ductal tissue. Other suitable laminarily organized luminal organs, tissue structure, or ductal tissues to which the present invention is directed include vas deferens, fallopian tubes, lacrimal ducts, trachea, stomach, intestines, vasculature, biliary duct, ductus ejaculatorius, ductus epididymidis, ductus parotideus, and surgically created shunts.

The method of the present invention in its broadest aspect encompasses as a first step providing a biocompatible synthetic or natural polymeric matrix that is shaped to conform to its use as a part or all of the luminal organ or tissue structure to be repaired, reconstructed, augmented or replaced. A biocompatible material is any substance not having toxic or injurious effects on biological function. The shaped matrix is preferably porous to allow for cell deposition both on and in the pores of the matrix. The shaped polymeric matrix is then contacted, preferably sequentially, with at least two different cell populations supplied to separate areas of the matrix (e.g., inside and outside) to seed the cell population on and/or into the matrix. The seeded matrix is then implanted in the body of the recipient where the separate, laminarily organized cell populations facilitate the formation of neo-organs or tissue structures.

In a preferred embodiment, the materials and methods of the invention are useful for the reconstruction or augmentation of bladder tissue. Thus, the invention provides treatments for such conditions as bladder exstrophy, bladder volume insufficiency, reconstruction of bladder following partial or total cystectomy, repair of bladders damaged by trauma, and the like.

While reference is made herein to augmentation of bladder according to the invention, it will be understood that the methods and materials of the invention are useful for tissue reconstruction or augmentation of a variety of tissues and organs in a subject. Thus, for example, organs or tissues such as bladder, ureter, urethra, renal pelvis, and the like, can be augmented or repaired with polymeric matrixes seeded with cells. The materials and methods of the invention further can be applied to the reconstruction or augmentation of vascular tissue (see, e.g., Zdrahala, R. J., J Biomater. Appl. 10 (4): 309-29 (1996)), intestinal tissues, stomach (see, e.g., Laurencin, C. T. et al., J Biomed Mater. Res. 30 (2): 133-8 1996), and the like. The patient to be treated may be of any species of mammals such as a dog, cat, pig, horse, cow, or human, in need of reconstruction, repair, or augmentation of a tissue.

Polymeric Matrices

Biocompatible material and especially biodegradable material is the preferred material for the construction of the polymeric matrix. The polymeric matrix is used in the construction of the reconstructive urothelial graft (RUG). The RUG is an implantable, biocompatible, synthetic or natural polymeric matrix with at least two separate surfaces. The RUG is shaped to conform to a at least a part of the luminal organ or tissue structure in need of treatment and has at least two different cell populations deposited in substantially separate areas either on or in the polymeric matrix. Thus the RUG is a laminarily organized matrix/cell construct.

Biocompatible refers to materials which do not have toxic or injurious effects on biological functions. Biodegradable refers to material that can be absorbed or degraded in a patient's body. Examples of biodegradable materials include, for example, absorbable sutures. Representative materials for forming the biodegradable structure include natural or synthetic polymers, such as, for example, collagen, poly(alpha esters) such as, poly(lactic acid), poly(glycolic acid), polyorthoesters and polyanhydrides and their copolymers, which degraded by hydrolysis at a controlled rate and are reabsorbed. These materials provide the maximum control of degradability, manageability, size and configuration. Preferred biodegradable polymer material include polyglycolic acid and polyglactin, developed as absorbable synthetic suture material. Polyglycolic acid and polyglactin fibers may be used as supplied by the manufacturer. Other biodegradable materials include cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

A presently preferred biocompatible polymer is Polyglactin, developed as absorbable synthetic suture material, a 90:10 copolymer of glycolide and lactide, manufactured as Vicryl<< braided absorbable suture (Ethicon Co., Somerville, N.J.) (Craig P. H., Williams J. A., Davis K. W., et al.: A Biological Comparison of Polyglactin 910 and Polyglycolic Acid Synthetic Absorbable Sutures. Surg. 141; 1010, (1975)) and polyglycolic acid. Polyglactin and polyglycolic acid fibers can be used as supplied by the manufacturer. The biocompatible polymer may be shaped using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the RUG. Next a solvent is used to dissolve away one of the components, resulting in pore formation. (See Mikos, U.S. Pat. No. 5,514,378, hereby incorporated by reference). In nucleation, thin films in the shape of a RUG are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a RUG structure with uniform pore sizes. Coating refers to coating or permeating a polymeric structure with a material such as, for example liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix may be weaved, compression molded and glued together. Furthermore different polymeric materials shaped by different processes may be joined together to form a composite shape. The composite shape may be a laminar structure. For example, a polymeric matrix may be attached to one or more polymeric matrixes to form a multilayer polymeric matrix structure. The attachment may be performed by gluing with a liquid polymer or by suturing. In addition, the polymeric matrix may be formed as a solid block and shaped by laser or other standard machining techniques to its desired final form. Laser shaping refers to the process of removing materials using a laser.

The biodegradable polymers can be characterized with respect to mechanical properties, such as tensile strength using an Instron tester, for polymer molecular weight by gel permeation chromatography (GPC), glass, transition temperature by differential scanning calorimetry (DSC) and bond structure by infrared (IR) spectroscopy; with respect to toxicology by initial screening tests involving Ames assays and in vitro teratogenicity assays and implantation studies in animals for immunogenicity, inflammation, release and degradation studies. In vitro cell attachment and viability can be assessed using scanning electron microscopy, histology and quantitative assessment with radioisotopes. The biodegradable material may also be characterized with respect to the amount of time necessary for the material to degrade when implanted in a patient. By varying the construction, such as, for example, the thickness and mesh size, the biodegradable material may substantially biodegrade between about 2 years or about 2 months, preferably between about 18 months and about 4 months, most preferably between about 15 months and about 8 months and most preferably between about 12 months and about 10 months. If necessary, the biodegradable material may be constructed so as not to degrade substantially within about 3 years, or about 4 years or about five or more years.

The polymeric matrix may be fabricated with controlled pore structure as described above. The size of the pores may be used to determine the cell distribution. For example, the pores on the polymeric matrix may be large to enable cells to migrate from one surface to the opposite surface. Alternatively, the pores may be small such that there is fluid communication between the two sides of the polymeric matrix but cells cannot pass through. Suitable pore size to accomplish this objective may be about 0.04 micron to about 10 microns in diameter, preferably between about 0.4 micron to about 4 microns in diameter. In some embodiments, the surface of the polymeric matrix may comprise pores sufficiently large to allow attachment and migration of a first population of cells into the pores. The pore size may be reduced in the interior of the polymeric matrix to prevent cells from migrating from one side of the polymeric matrix to the opposite side. On the opposite side of the polymeric matrix, the pores may again enlarge to allow the attachment and establishment of a second population of cells. Because of the reduced pore size in the interior of the polymeric matrix, the first cell population and the second cell population initially cannot mix. One embodiment of a polymeric matrix with reduced pore size is a laminated structure of a small pore material sandwiched between two large pore material. Alternatively, a large pore material laminated to a small pore material may also allow cells to establish growth on both sides without any intermixing of cells. Polycarbonate membranes are especially suitable because they can be fabricated in very controlled pore sizes such as, for example, about 0.01 microns, about 0.05 micron, about 0.1 micron, about 0.2 micron, about 0.45 micron, about 0.6 micron, about 1.0 micron, about 2.0 microns and about 4.0 microns. At the submicron level the polymeric matrix may be impermeable to bacteria, viruses and other microbes. At the present time, a mesh-like structure formed of fibers, which may be round, scalloped, flattened, star shaped, solitary or entwined with other fibers is preferred. The use of branching fibers is based upon the same principles which nature has used to solve the problem of increasing surface area proportionate to volume increases. All multicellular organisms utilize this repeating branching structure. Branching systems represent communication networks between organs, as well as the functional units of individual organs. Seeding and implanting this configuration with cells allows implantation of large numbers of cells, each of which is exposed to the environment of the host, providing for free exchange of nutrients and waste while neovascularization is achieved. The polymeric matrix may be made flexible or rigid, depending on the desired final form, structure and function.

In one preferred embodiment, the polymeric matrix is formed with a polyglycolic acid with an average fiber diameter of 15 μM and configured into a bladder shaped mold using 4-0 polyglactin 910 sutures. The resulting structure is coated with a liquefied copolymer, such as, for example, poly-DL-lactide-co-glycolide 50:50, 80 illigram per milliliter methylene chloride, in order to achieve adequate mechanical characteristics and to set its shape.

Polymeric matrixes can be treated with additives or drugs prior to implantation (before or after the polymeric matrix is seeded with cells, if the optional seeded cells are employed), e.g., to promote the formation of new tissue after implantation. Thus, for example, growth factors, cytokines, extracellular matrix components, and other bioactive materials can be added to the polymeric matrix to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. Vet. Surg. 24 (5): 408-19 (1995)). For example, when polymeric matrizes (optionally seeded with endothelial cells) are used to augment vascular tissue, vascular endothelial growth factor (VEGF), (see, e.g., U.S. Pat. No. 5,654,273) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the polymeric matrix, if added cells are employed. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

One preferred supporting matrix is composed of crossing filaments which can allow cell survival by diffusion of nutrients across short distances once the cell support matrix is implanted. The cell support matrix becomes vascularized in concert with expansion of the cell mass following implantation.

The building of three-dimensional structure constructs in vitro, prior to implantation, facilitates the eventual terminal differentiation of the cells after implantation in vivo, and minimizes the risk of an inflammatory response towards the matrix, thus avoiding graft contracture and shrinkage.

The polymeric matrix may be shaped into any number of desirable configurations to satisfy any number of overall system, geometry or space restrictions. For example, in the use of the polymeric matrix for bladder reconstruction, the matrix may be shaped to conform to the dimensions and shapes of the whole or a part of a bladder. Naturally, the polymeric matrix may be shaped in different sizes and shapes to conform to the bladders of differently sized patients. Optionally, the polymeric matrix should be shaped such that after its biodegradation, the resulting reconstructed bladder may be collapsible when empty in a fashion similar to a natural bladder. The polymeric matrix may also be shaped in other fashions to accommodate the special needs of the patient. For example, a previously injured or disabled patient, may have a different abdominal cavity and may require a bladder reconstructed to adapt to fit. In other embodiments of the invention, the polymeric matrix is used for the treatment of laminar structures in the body such as urethra, vas deferens, fallopian tubes, lacrimal ducts. In those applications the polymeric matrix may be shaped as a hollow tube.

The polymeric matrix may be sterilized using any known method before use. The method used depend on the material used in the polymeric matrix. Examples of sterilization methods include steam, dry heat, radiation, gases such as ethylene oxide, gas and boiling.

Harvesting Cells for the Reconstructive Urothelial Graft (RUG)

The RUG is constructed in part using urothelial cells and smooth muscle cells from a donor. One advantage of the methods of the invention is that because of the rapid growth of the urothelial and smooth muscle cells, sufficient cells for the construction of a RUG may be grown in less than 5 weeks. In an autologous RUG, the cells may be derived from the patient's own tissue such as, for example, from the bladder, urethra, ureter, and other urogenital tissue. In an allogeneic RUG, the cells may be derived from other member of the patient's species. In a xenogenic RUG, the cells may be derived from a species different from the patient. Donor cells may be from any urothelial cells and smooth muscle cells origin and from any mammalian source such as, for example, humans, bovine, porcine, equine, caprine and ovine sources. Urothelial cells and smooth muscle cells may be isolated in biopsies, or autopsies. In addition, the cells may be frozen or expanded before use.

To prepare for RUG construction, tissue containing urothelial and smooth muscle cells is dissociated separately into two cell suspensions. Methods for the isolation and culture of cells were discussed in issued U.S. Pat. No. 5,567,612 which is herein specifically incorporated by reference. Dissociation of the cells to the single cell stage is not essential for the initial primary culture because single cell suspension may be reached after a period, such as, a week, of in vitro culture. Tissue dissociation may be performed by mechanical and enzymatic disruption of the extracellular matrix and the intercellular junctions that hold the cells together. Urothelial cells and smooth muscle cells from all developmental stages, such as, fetal, neonatal, juvenile to adult may be used.

Cells (such as autologous cells) can be cultured in vitro, if desired, to increase the number of cells available for seeding on the polymeric matrix "scaffold." The use of allogenic cells, and more preferably autologous cells, is preferred to prevent tissue rejection. However, if an immunological response does occur in the subject after implantation of the RUG, the subject may be treated with immunosuppressive agents such as, for example, cyclosporin or FKSO6, to reduce the likelihood of rejection of the RUG. In certain embodiments, chimeric cells, or cells from a transgenic animal, can be seeded onto the polymeric matrix.

Cells may be transfected prior to seeding with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery. Urothelial and muscle cells could be transfected with specific genes prior to polymer seeding. The cell-polymer construct could carry genetic information required for the long term survival of the host or the tissue engineered neo-organ. For example, cells may be transfected to express insulin for the treatment of diabetes.

Cell cultures may be prepared with or without a cell fractionation step. Cell fractionation may be performed using techniques, such as florescent activated cell sorting, which is known to those of skill in the art. Cell fractionation may be performed based on cell size, DNA content, cell surface antigens, and viability. For example, urothelial cells may be enriched and smooth muscle cells and fibroblast cells may be reduced for urothelial cell collection. Similarly, smooth muscle cells may be enriched and urothelial cells and fibroblast cells may be reduced for smooth muscle cell collection. While cell fractionation may be used, it is not necessary for the practice of the invention.

Cell fractionation may be desirable, for example, when the donor has diseases such as bladder cancer or metastasis of other tumors to the bladder. A bladder cell population may be sorted to separate malignant bladder cells or other tumor cells from normal noncancerous bladder cells. The normal noncancerous bladder cells, isolated from one or more sorting techniques, may then be used for bladder reconstruction.

Another optional procedure in the method is cryopreservation. Cryogenic preservation may be useful, for example, to reduce the need for multiple invasive surgical procedures. Cells taken from a bladder may be amplified and a portion of the amplified cells may be used and another portion may be cryogenically preserved. The ability to amplify and preserve cells allow considerable flexibility in the choice of donor cells. For example, cells from a histocompatible donor, may be amplified and used in more than one recipient.

Another example of the utility of cryogenic preservation is in tissue banks. Donor cells may be cryopreserved along with histocompatibility data. Donor cells may be stored, for example, in a donor tissue bank. As tissue is needed for bladder reconstruction, cells may be selected which are most histocompatible to the patient. Patients who have a disease or undergoing treatment which may endanger their bladders may cryogenically preserve a biopsy of their bladders. Later, if the patient's own bladder fails, the cryogenically preserved bladder cells may be thawed and used for treatment. For example, if bladder cancer reappeared after bladder reconstruction, cryogenically preserved cells may be used for bladder reconstruction without the need isolate more tissue from the patient for culture.

Seeding

Seeding of cells onto the polymeric matrix can be performed, e.g., as is described in the Example or according to standard methods. For example, the seeding of cells onto polymeric substrates for use in tissue repair has been reported (see, e.g., Atala, A. et al., J. Urol. 148(2 Pt 2): 658-62 (1992); Atala, A., et al. J. Urol. 150 (2 Pt 2): 608-12 (1993)). Cells grown in culture can be trypsinized to separate the cells, and the separated cells can be seeded on the polymeric matrix. Alternatively, cells obtained from cell culture can be lifted from a culture plate as a cell layer, and the cell layer can be directly seeded onto the polymeric matrix without prior separation of the cells.

In a preferred embodiment, at least 50 million cells are suspended in media and applied to each square centimeter of a surface of a polymeric matrix. The polymeric matrix is incubated under standard culturing conditions, such as, for example, 37. degree. 5% $CO_2$, for a period of time until the cells attached. However, it will be appreciated that the density of cells seeded onto the polymeric substrate can be varied. For example, greater cell densities promote greater tissue formation by the seeded cells, while lesser densities may permit relatively greater formation of tissue by cells infiltrating the graft from the host. Other seeding techniques may also be used depending on the polymeric matrix and the cells. For example, the cells may be applied to the polymeric matrix by vacuum filtration. Selection of cell types, and seeding of cells onto a polymeric matrix, will be routine to one of ordinary skill in the art in light of the teachings herein.

In an embodiment of the invention, a polymeric matrix is seeded on two sides with two different populations of cells. This may be performed by first seeding one side of the polymeric matrix and then seeding the other side. For example, the polymeric matrix may be placed with one side on top and seeded. Then the polymeric matrix may be repositioned so that a second side is on top. The second side may then be seeded with a second population of cells. Alternatively, both sides of the polymeric matrix may be seeded at the same time. For example, two cell chambers may be positioned on both sides (i.e., a sandwich) of the polymeric matrix. The two chambers may be filled with different cell populations to seed both sides of the polymeric matrix simultaneously. The sandwiched polymeric matrix may be rotated, or flipped frequently to allow equal attachment opportunity for both cell populations. Simultaneous seeding may be preferred when the pores of the polymeric matrix are sufficiently large for cell passage from one side to the other side. Seeding the polymeric matrix on both sides simultaneously will reduce the likelihood that the cells would migrate to the opposite side.

In another embodiment of the invention, two separate polymeric matrixes may be seeded with different cell populations. After seeding, the two matrixes may be attached together to form a single polymeric matrix with two different cell populations on the two sides. Attachment of the matrixes to each other may be performed using standard procedures such as fibrin glue, liquid co-polymers, sutures and the like.

Surgical Reconstruction.

Grafting of polymeric matrixes to an organ or tissue to be augmented can be performed according to the methods described in the Examples or according to art-recognized methods. As shown in the examples, the polymeric matrix can be grafted to an organ or tissue of the subject by suturing the graft material to the target organ.

The techniques of the invention may also be used to treat cancer of the bladder. For example, a normal bladder tissue sample may be excised from a patient suffering from bladder cancer. Urothelial cells and smooth muscle cells from the tissue sample may be cultured for a period of time in vitro and expanded. The cells may be sorted using a florescent activated cell sorter to remove cancerous or precancerous cells. The sorted cells may be used to construct a RUG. At the same time, the patient may be treated for cancer. Cancer treatment may involve excision of the cancerous part of the bladder in addition to chemotherapy or radiation treatment. After the cancer treatment, the RUG may be used to reconstruct the bladder.

While a method for bladder reconstruction is disclosed in the Example, other methods for attaching a graft to an organ or tissue of the subject (e.g., by use of surgical staples) may also be employed. Such surgical procedures can be performed by one of ordinary skill in the art according to known procedures.

As a result of these benefits, the present method of bladder reconstructive surgery is suitable for bladder tissue repair under numerous circumstances. As described above the bladder graft may be used to repair a deteriorated bladder due to.

Other embodiments and advantages of the invention are set forth, in part, in the description which follows and, in part, will be obvious from this description and may be learned from practice of the invention.

EXAMPLES

Example 1

Creation of Bladder-Shaped Polymers

A synthetic polymer matrix of polyglycolic acid with an average fiber diameter of about 15 .mu.m and an interfiber distance between about 0 to about 200 . mu.m and dimensions of about 10 cm by about 10 cm was configured into a bladder shaped mold using biodegradable 4-0 olyglactin 910 sutures. The resulting flexible scaffold was coated with a liquefied copolymer, a mixture of about 50% poly-DL-lactide-co-glycolide and about 50% 80 mg/ml methylene chloride, in order to achieve adequate mechanical characteristics. After sterilization with ethylene oxide, the polymers were stored in a desiccator.

Example 2

Cell Harvest and Culture

A total of 14 beagle dogs underwent a trigone-sparing cystectomy. The animals were randomly assigned to one of three groups. Two were assigned to Group A and underwent closure of the trigone without a reconstructive procedure. Six were assigned to Group B and underwent bladder reconstruction with a cell-free bladder shaped biodegradable polymer. Six were assigned to Group C and underwent bladder reconstruction using a prefabricated tissue engineered neo-organ. The neo-organ comprises a bladder shaped biodegradable polymer with autologous urothelial cells attached to the luminal surface and smooth muscle cells attached to the exterior surface. The cell populations had been separately expanded from a previously harvested autologous transmural bladder specimen.

The six animals in group C, which were to be reconstructed with a tissue engineered neo-organ, underwent a transmural bladder biopsy of about one square centimeter which was harvested from the vesical dome via a minimal suprapubic midline incision under general anesthesia. The defect was closed with a 4-0 polyglactin 910 suture. The bladder specimens were kept in prewarmed keratinocyte medium, and cell harvest for in-vitro cultures was initiated immediately after tissue excision.

Urothelial and smooth muscle cell populations, dissociated from the one square centimeter bladder biopsies, could be routinely expanded and passaged separately. The average time elapsed between the initial bladder biopsy and final implantation of the tissue engineered neo-organs was 32+/−2.8 days (Mean+SD). Approximately thirty-two 25 cm plates of each cell type, muscle and urothelial cells, containing approximately $10^7$ cells per plate, were processed to constitute one tissue engineered neo-organ.

The harvested cells were cultured according to previously published protocols of Atala et al., (J. Urol. 150: 608, 1993) and Cilento et al., (J. Urol. 152: 655, 1994.) which are herein specifically incorporated by reference. The urothelial and muscular layers of the bladder biopsy were microsurgically detached from each other and processed separately. Briefly, the dissected smooth muscle tissue was cut into cubes of about one millimeter and primarily plated on a 10 cm tissue culture petri dish. Smooth muscle cultures were maintained and expanded with Dulbeccos's Modified Eagles Medium (DMEM, Sigma, St. Louis, Mo.) supplemented with 10% fetal calf serum (Biowhittaker Inc., Walkersville, Md.). Urothelial cells were also dissected into one millimeter cubes and plated on 24 well plates. Urothelial cultures were maintained and expanded with serum-free keratinocyte growth medium supplemented with about 5 ng/ml of epidermal growth factor and about 50 . mu.g/ml of bovine pituitary extract (Gibco BRL, Life Technologies, Grand Island, N.Y.). All cell cultures were incubated at 37. degree. C. in a humidified atmosphere maintained at about 5% level of carbon dioxide. Medium was changed twice weekly. For cell passage cultures at about 80% confluence were trypsinized by incubation for 5 minutes in 0.05% trypsin in 1 millimole ethylenediaminetetraacetic acid. After this period soybean trypsin inhibitor, at 2 units per unit of trypsin, was added to the cell suspension. Both urothelial and smooth muscle cells were expanded separately until sufficient cell quantities were available for a seeding density of approximately one million cells per square centimeter of polymer surface.

Example 3

Cell Seeding on Polymer Scaffold

For each tissue engineered neo-organ, about 32 confluent 25 cm plates of each cell type, muscle and urothelium, were processed for seeding. Muscle cell cultures were trypsinized, collected, washed and combined in one tube. The exterior surface of the pre-molded bladder shaped polymer matrix was seeded with the resuspended smooth muscle cell population. The cell-seeded polymers were incubated in Dulbeccos's Modified Eagles Medium (DMEM, Sigma, St. Louis, Mo.) supplemented with 10% fetal calf serum (Biowhittaker Inc., Walkersville, Md.). The medium was changed at 12 hour intervals to ensure sufficient supply of nutrients. After 48 hours of incubation, the urothelial cells were processed in a similar fashion and were seeded onto the luminal surface of the polymer.

Example 4

Bladder Reconstruction

Following pretreatment with intramuscular injection of 0.1 mg of acepromazine for every kilogram of body weight, surgery was performed under intravenous pentobarbital anesthesia of about 25 to about 35 mg per kilogram of body weight with endotracheal aeration. About 500 mg of Cefazolin sodium was administered intravenously both preoperatively and intraoperatively. Additional treatment of subcutaneously Cefazolin sodium was administered for 5 postoperative days at a dose of about 30 milligrams per kilogram body weight per day. Postoperative analgesic treatment was managed with subcutaneous injections of about 0.1 to about 0.6 milligrams of butorphanol per kilogram of body weight.

Figure 1B:
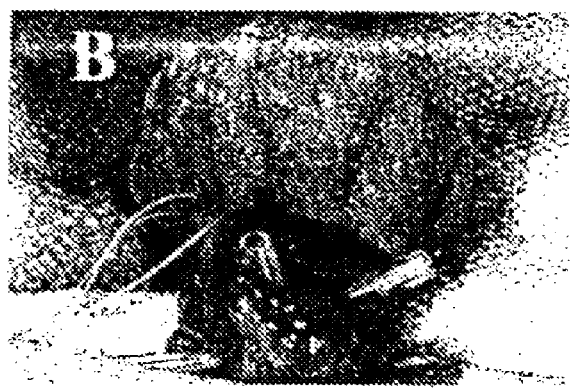
Figure 1C:

As shown in FIG. 1A, a midline laparotomy was performed, the bladder was exposed (FIG. 1A) and both ureters were identified. The bladder wall was incised ventrally and both ureteric junctions were visualized and temporarily intubated with 4 F stents. A subtotal cystectomy was performed, sparing the trigone area bearing the urethra and ureteral junctions. Care was taken not to compromise or obstruct the ureters. In two animals the trigone was closed, without any polymer graft, with two layers of 4-0 vicryl. As depicted in FIG. 1B, 12 animals undergone an anastomosis between the bladder shaped polymer matrix and the trigone with interlocking running sutures of 4-0 vicryl. Of the 12 animals, 6 received a bladder shaped polymer alone, and six received a bladder shaped polymer coated with cells. A 10 F silicone catheter was inserted into the urethra from the trigone in a retrograde fashion. An 8 F suprapubic catheter was brought into the bladder lumen passing through a short submucosal tunnel in the trigonal region. The suprapubic catheter was secured to the bladder serosa with a pursestring suture of 4-0 chromic. The anastomosis between trigone and graft was marked at each quadrant with permanent polypropylene sutures for future graft site identification. The neo-bladder was covered with fibrin glue (Vitex Technologies Inc., New York, N.Y.). As depicted in FIG. 1C, omentum was wrapped and secured around the neo-reservoir. The abdomen was closed with three layers of 3-0 vicryl. After recovery from anesthesia, all animals wore restraint collars to avoid wound and catheter manipulation during the early postoperative period. The transurethral catheters were removed between postoperative days 4 and 7. Cystograms were performed about four weeks postoperatively, immediately prior to the suprapubic catheter removal. Cystograms and urodynamic studies were serially performed at about 1, about 2, about 3, about 4, and 6 and about 11 months after surgery.

Example 5

Analysis of Reconstructed Bladder

Urodynamic studies and radiographic cystograms were performed preoperatively and postoperatively at about 1, about 2, about 3, about 4, about 6, and about 11 months after surgery. The two animals who underwent closure of the trigone without a reconstructive procedure were sacrificed at about 11 months. Animals from the remaining two experimental groups were sacrificed at about 1, about 2, about 3, about 4, about 6 and about 11 months after surgery. Bladders were retrieved for gross, histological and immunocytochemical analyses.

Urodynamic studies were performed using a 7 F double-lumen transurethral catheter. The bladders were emptied and intravesical pressures were recorded during instillation of prewarmed saline solution at constant rates. Recordings were continued until leak point pressures (LPP) were reached. Bladder volume at capacity ($Vol._{max}$), LPP and bladder compliance ($Vol._{max}/LPP$) were documented. Bladder compliance, also called bladder elastance, denotes the quality of yielding to pressure or force without disruption. Bladder compliance is also an expression of the measure of the ability to yield to pressure or force without disruption, as an expression of the distensibility of the bladder. It is usually measured in units of volume change per unit of pressure change. Subsequently, radiographic cystograms were performed. The bladders were emptied and contrast medium was instilled intravesically under fluoroscopic control.

Urodynamic Results

Prior to trigone-sparing cystectomy, the animals of groups A, B and C did not significantly differ in preoperative mean bladder capacity (78+/−16 ml, 63+/−22 ml, 69+/−8 ml, p=0.44, [Means +/−A SD]) or preoperative bladder compliance (2.6+/−0.2 ml/cm $H_2O$, 2.2+/−1.2 ml/cm $H_2O$, 2.1+/−1.1 ml/cm $H_2O$, p=0.85, [Means +/−SD]).

Figure 2A:
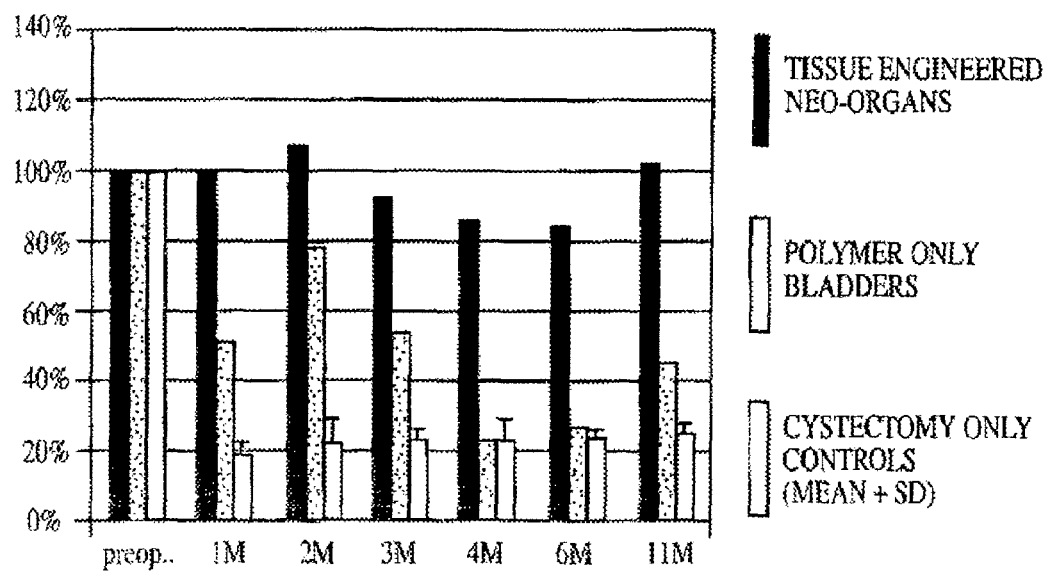
FIG. 2 depicts (A) bladder capacities and (B) compliance at different postoperative time points relative to preoperative capacities of 100%.

Both control animals, which did not undergo reconstruction after subtotal cystectomy, could only maintain 22% (+/−2%) of the native capacity during the observed period. A pattern of frequent voiding was obvious in these animals. The animals reconstructed with cell-free polymers developed mean bladder capacities of 46% (+/−20%) of preoperative values. A mean bladder capacity of 95% (+/−9%) of the original pre-cystectomy volume was achieved by the tissue engineered bladder replacements (FIG. 2A).

Figure 2B:
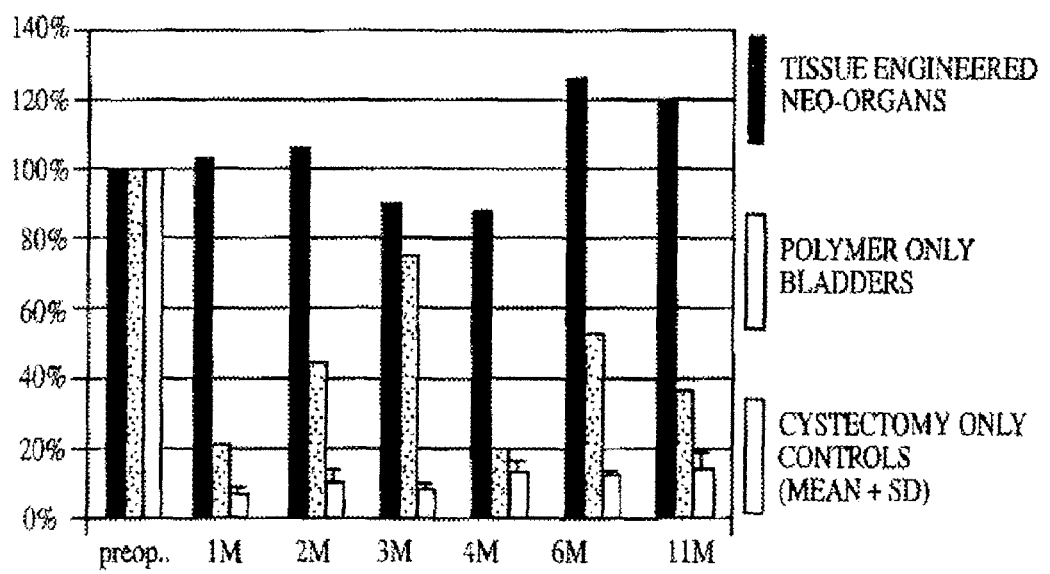

The subtotal cystectomy bladders which were not reconstructed showed a pronounced reduction in bladder compliance to mean values of 10% (+/−3%) of the preoperative values. All polymer only implants without cells also had a considerable loss of compliance. At various time points of sacrifice, bladder compliances were reduced to an average of 42% (+/−21%) of the preoperative values. The compliance of the tissue engineered bladders showed almost no difference from the preoperative values measured when the native bladder was present (106%+/−16%, FIG. 2B).

Figure 3A:
FIG. 3 depicts radiographic cystograms 11 months after subtotal cystectomy followed by (A) Subtotal cystectomy without reconstruction (Group A); (B) Polymer only implant (Group B); and (C) tissue engineered neo-organ (Group C).
Figure 3B:
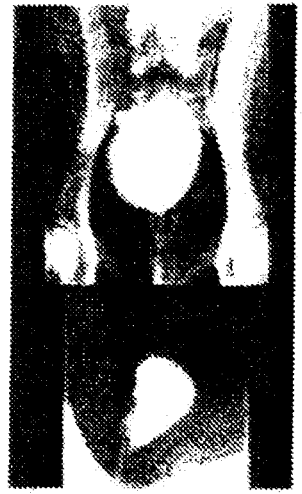
Figure 3C:
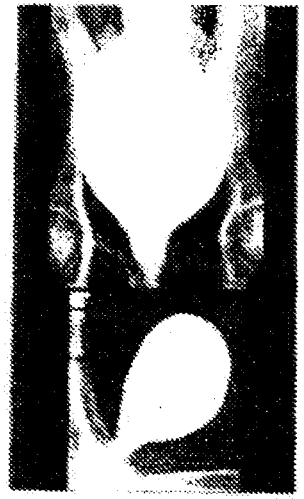

Clinically, all animals had a stable course after bladder reconstruction, were able to void spontaneously upon catheter removal and survived their intended study periods. One month after surgery, the radiographic cystograms showed a watertight reservoir in all animals. Cystograms of the subtotal cystectomy only animals showed that unaugmented trigones were only able to regenerate minimal reservoir capacities throughout the study period. The polymer only implants demonstrated signs of partial graft collapse. The tissue engineered bladders were fully distendable and their contour could be delineated from the native trigone. During follow-up cystograms, the polymer only implants continued to show smaller sized reservoirs while the tissue engineered bladders appeared normal in size and configuration (FIG. 3).

Example 6

Gross Findings

At the intended time points, the animals were euthanized by intravenous pentobarbital administration The internal organs and the urogenital tract were inspected for gross abnormalities. The bladder was retrieved and the marking sutures identifying the transition zone between native trigone and graft were exposed. Cross sections were taken from within the native trigone, the outlined transition zone and the proximally located neo-bladder.

Figure 4A:
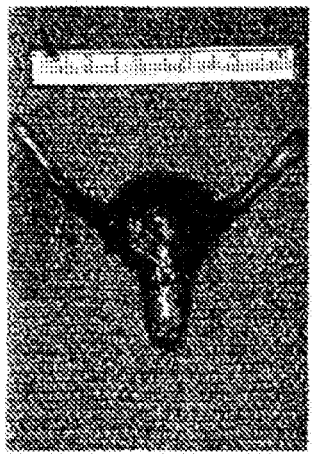
FIG. 4 depicts (A and B) gross aspect of subtotal cystectomy control; (C and D) polymer only implant; and (E and F) tissue engineered neo-organ retrieved after 11 months.
Figure 4B:
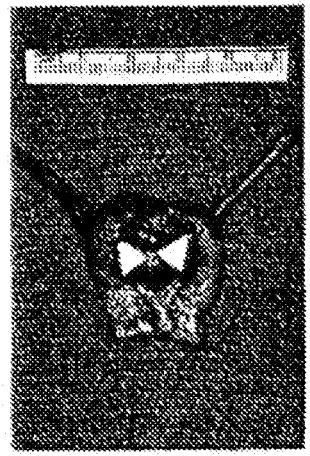

Trigone-Sparing Cystectomy only (Group A). The reservoirs appeared small, but normal in appearance (FIGS. 4A and B).

Figure 4C:
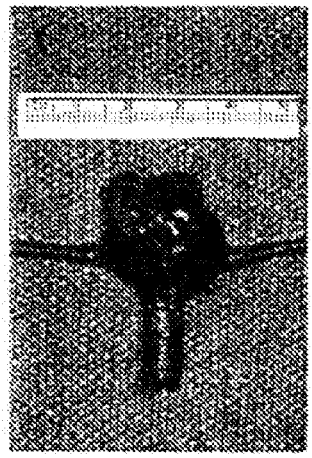
Figure 6A:
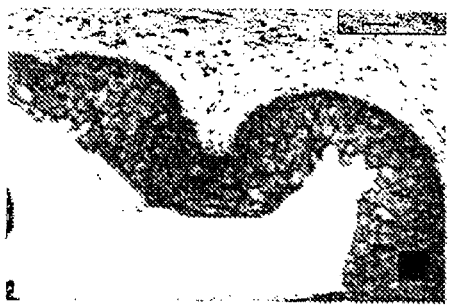
FIG. 6 depicts positive immunocytochemical staining of tissue engineered neo-organ for (A) pancytokeratins AE1/AE3; (B) Urothelial differentiation related membrane proteins; (C) smooth muscle actin; and (D) S-100 antibodies six months after implantation.
Figure 6B:
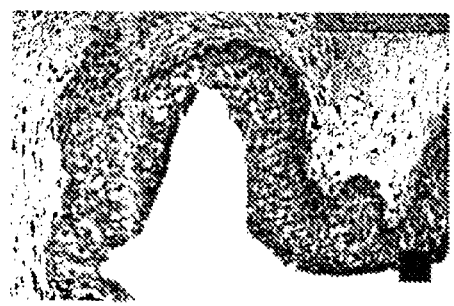
Figure 6C:
Figure 6D:

Polymer only Bladders (Group B): Gross inspection of the cell-free polymer implant retrieved at one month showed that the original spherical architecture of the polymer had partially collapsed. A solitary, asymptomatic bladder stone of 11 mm was found in the 2 month time point, representing the only incidence of lithogenesis in this study. At the two month time point, graft shrinkage of approximately 50% was macroscopically obvious at necropsy. The bladders retrieved at 4, 6 and 11 months contained progressive formations of thick scar tissue at the dome and were firmly covered with adherent omentum (FIGS. 4C and D). By 11 months, graft shrinkage of over 90% was obvious macroscopically. The initially placed polypropylene marking sutures were noted in the area of the trigone, adjacent to the scar tissue. Approximately 10% of the total bladder area was above the marking sutures.

Tissue Engineered Neo-Organs (Group C): Autopsy exploration showed no signs of upper tract obstruction, lithogenesis, encrustration or other abnormalities for all investigated time points. At one month, the polymer scaffold inside the omentum-wrapped tissue engineered neo-bladder remained visually and palpably identifiable. The neo-bladders had a flexible, and distendable configuration. At 6 and 11 months, omental adhesions could be bluntly separated from the bladder dome, and a serosa-like layer had regenerated over the tissue engineered neo-organ (FIGS. 4E). The initially placed polypropylene marking sutures were noted in the distal region of the bladder, at the level of the trigone. Approximately 70% of the total bladder area was above the marking sutures. Upon entering the bladder ventrally, a smooth mucosal surface was noted, without any differences between the native and tissue engineered bladder (FIG. 4F).

During the duration of the study, none of the dogs demonstrated any untoward 30 effects. All animals survived until the time of sacrifice without any noticeable complications such as urinary tract infection or calculi formation. Fluoroscopic cystography of all the augmented bladders showed a normal bladder configuration without any leakage at one, two and three months after the procedure. At retrieval, the augmented bladders appeared grossly normal without any evidence of diverticular formation in the region of the graft. The thickness of the grafted segment was similar to that of the native bladder tissue. There was no evidence of adhesion or fibrosis. Histologically, all retrieved bladders contained a normal cellular organization consisting of a urothelial lined lumen surrounded by submucosal tissue and smooth muscle. An angiogenic response was evident in all specimens.

Example 7

Histological and Immunocytochemical Findings

Specimens were fixed in 10% buffered formalin and processed. Tissue sections were cut at about 4 to about 6 microns for routine staining with Hematoxylin and Eosin (H&E) and Masson's trichrome. Immunocytochemical staining methods were employed with several specific primary antibodies in order to characterize urothelial and smooth muscle cell differentiation in the retrieved bladders. Anti-Desmin antibody (monoclonal NCL-DES-DERII, clone DE-R-11, Novocastra.RTM., Newcastle UK), which reacts with parts of the intermediate filament muscle cell protein desmin, and Anti-Alpha Smooth Muscle Actin antibody (monoclonal NCL-SMA, clone asm-1, Novocastra.RTM., Newcastle UK), which labels bladder smooth muscle actin, were used as general markers for smooth muscle differentiation. Anti-Pancytokeratins AE1/AE3 antibody (monoclonal, Cat. No. 1124 161, Boehringer Mannheim.RTM.) and Anti-Cytokeratin 7 antibody (NCL-CK7, Clone LP5K, IgG2b, Novocastra.RTM., New Castle, UK) which react against intermediate filaments that form part of the cytoskeletal complex in epithelial tissues, were used to identify urothelium. Anti-Asymmetric Unit Membrane (AUM) staining, using polyclonal antibodies, was used to investigate the presence of mammalian uroplakins, which form the apical plaques in mammalian urothelium and play an important functional role during advanced stages of urothelial differentiation. Anti S-100 antibody (Sigma.RTM., St. Louis Mo., No. IMMH-9), reacting with the acidic calcium-binding protein S-100, mainly present in Schwann cells and glial elements in the nervous system, was used to identify neural tissues.

Specimens were fixed in Carnoy's solution and routinely processed for immunostaining. High temperature antigen unmasking pretreatment with about 0.1% trypsin was performed using a commercially available kit according to the manufacturer's recommendations (Sigma.RTM., St. Louis Mo., T-8 128). Antigen-specific primary antibodies were applied to the deparaffinized and hydrated tissue sections. Negative controls were treated with plain serum instead of the primary antibody. Positive controls consisted of normal bladder tissue. After washing with phosphate buffered saline, the tissue sections were incubated with a biotinylated secondary antibody and washed again. A peroxidase reagent was added and upon substrate addition, the sites of antibody deposition were visualized by a brown precipitate. Counterstaining was performed with Gill's hematoxylin.

Trigone-Sparing Cystectomy only (Group A): The trigone-sparing cystectomy organs showed a normal histological architecture which was confirmed by immunocytochemical staining.

Polymer only Bladders (Group B): The polymers implanted without cells were found to undergo a fibrovascular reaction consisting of fibroblast deposition and extensive recruitment of inflammatory cells, including macrophages, and ubiquitous signs of angiogenesis at one month. Epithelial coverage was evident throughout the entire polymer. The epithelium stained positive for the broadly reacting anti-pan-cytokeratins AE1/AE3, anti-cytokeratin 7, and the urothelium specific anti-AUM. Fibrotic tissue deposition was noted at the sites of polymer degradation. The 2, 3 and 4 month time points showed extension of the native submucosal and muscular layer of the trigone onto the fibrotic polymer region at the transition zone. In the 6 and 11 month specimens abundant connective tissue formation had replaced the fully degraded polymer fibers of the proximally located neo-bladder region. Smooth muscle alpha actin positive cells were only scarcely evident in this region.

Tissue Engineered Neo-Organs (Group C): The tissue engineered neo-organ retrieved at one month showed complete luminal coverage with urothelium. The epithelium stained positive for the broadly reacting anti-pancytokeratins AE1/AE3, anti-cytokeratin 7, and the urothelium specific anti-AUM. The polymer fibers carried cell formations staining positive for .alpha. smooth muscle actin. An adequate angiogenic response was evident. At two months, before the polymers underwent complete biodegradation, the muscle fibers had a spatial alignment, forming variably sized bundles. By three months, there was complete polymer degradation and a tri-layered structure was evident in the proximally located neo-bladder region, consisting of a morphologically normal uroepithelial lining over a sheath of submucosa, followed by a layer containing multiform smooth muscle bundles. Six months postoperatively, an ingrowth of neural tissue was present for the first time as evidenced by S-100 staining. Bladders were found to have matured towards a normal histological and phenotypic structure as evidenced by its staining with hematoxylin and eosin, trichrome, alpha smooth muscle actin, desmin, pancytokeratins AE1/AE3, cytokeratin 7 and AUM antibodies (FIGS. 5 and 6). Histologically and immunocytochemically, there were no marked differences present between the 6 month and 11 month time point bladders.

Example 8

Statistical Findings

Statistical evaluations were performed on the measurements using a two-tailed student's t-test with p-values of less than or equal to 0.05 considered significant. The cystectomy only controls and polymer only grafts maintained average capacities of 22% and 46% of preoperative values, respectively. An average bladder capacity of 95% of the original pre-cystectomy volume was achieved in the tissue-engineered bladder replacements. The subtotal cystectomy reservoirs which were not reconstructed and polymer only reconstructed bladders showed a marked decrease in bladder compliance (10% and 42%). The compliance of the tissue engineered bladders showed almost no difference from pre-operative values that were measured when the native bladder was present (106%). Histologically, the polymer only bladders presented a pattern of normal urothelial cells with a thickened fibrotic submucosa and a thin layer of muscle fibers. The retrieved tissue engineered bladders showed a normal cellular organization, consisting of a tri-layer of urothelium, submucosa and muscle. Immunocytochemical analyses for desmin, .alpha.-actin, cytokeratin 7, pancytokeratins AE1/AE3 and uroplakin III confirmed the muscle and urothelial phenotype. S-100 staining indicated the presence of neural structures.

The animals which had undergone the trigone-sparing cystectomy and were closed primarily gained a minimal amount of reservoir volume over time but did not approach the pre-cystectomy values. The free graft polymer only bladders had a slight increase in volume and developed fibrotic neo-bladders, which had a well developed urothelial layer, but a markedly deficient muscular architecture, and were associated with a reduced compliance curve. The tissue aneroid neo-bladders were able to approach and surpass the pre-cystectomy bladder capacities. The compliance of these bladders approached the pre-cystectomy values at each time point, including the four week postoperative examination. The retrieved tissue engineered bladders showed a normal cellular organization, consisting of a tri-layer of urothelium, submucosa and muscle. Inmunocytochemical analysis with desmin and smooth muscle alpha actin confirmed the muscle phenotype. Pancytokeratins AE1/AE3, cytokeratin 7, and uroplakin III could be demonstrated by immunohistochemistry, confirming the urothelial phenotype. Positive S-100 staining suggested, that an ingrowth of neural structures into the tissue engineered bladders is possible. The tissue engineered neo-bladders were able to function normally soon after implantation. Structurally and functionally, they were indistinguishable from native bladders. Our results show, for the first time, that creation of a tri-layered structure, composed of bladder muscle and urothelium in vitro, is beneficial for the ultimate functional results of bladder tissue created de-novo. Our results of bladder replacement with the cell-free polymer graft are consistent with prior reports in the literature over the last several decades regarding free grafts. When other materials are used as free grafts without cells, the different histological components may be present, but are not necessarily fully developed or functional. Furthermore, the results of the cell-free polymer bladder control group are consistent with the literature in terms of graft contracture and shrinkage over time. The second control group, which underwent primary closure after cystectomy, clearly indicated that the increase in capacity in the tissue engineered neo-bladders was due mostly to the implant and not to the natural regenerating and elastic features of the native canine bladders. The results show that bladder submucosa seeded with urothelial and muscle cells can form new bladder tissue which is histologically and functionally indistinguishable from the native bladder. This result may be due to a possible maintenance of the architectural form of the bladder by the extracellular matrix regenerated by the seeded cells. The urothelial and muscle cells seeded on the polymeric matrix appear to prevent the resorption of the graft. This technology is able to form new bladder tissue which is anatomically and functionally similar to that of normal bladders.

Other embodiments and uses of the invention will be apparent to those skilled in the art from consideration of the specification and practice of the invention disclosed herein. All U.S. Patents and other references noted herein for whatever reason are specifically incorporated by reference. The specification and examples should be considered exemplary only with the true scope and spirit of the invention indicated by the following claims.

The invention claimed is:

1. A method for preparing a device for the replacement or repair of a bladder, or portion of a bladder, in a human comprising:
    a. providing an implantable, biocompatible, synthetic or natural, polymeric matrix structure in the shape of a bladder or portion of a bladder having at least two separate surfaces, wherein the polymeric matrix structure is coated with a biodegradable shape-setting material comprising a liquefied poly-DL-lactide-co-glycolide copolymer;
    b. depositing at least a first cell population on or in said polymeric matrix structure to form an organized matrix/cell construct.

2. The method of claim 1, wherein the first cell population deposited is substantially a urothelial cell population.

3. The method of claim 1, wherein the first cell population deposited is substantially a smooth muscle cell population.

4. The method of claim 1, further comprising depositing a second cell population on or in said polymeric matrix, wherein the second cell population is of a different cell type than the first cell population.

5. The method of claim 4, wherein the first and the second cell populations are deposited sequentially.

6. The method of claim 4, wherein the first cell population deposited is substantially smooth muscle cells.

7. The method of claim 4, wherein the second cell population deposited is substantially urothelial cells.

8. The method of claim 4, wherein the second cell population is substantially urothelial cells that are deposited on an inner surface of said polymeric matrix structure and the first cell population is substantially smooth muscle cells that are deposited on an outer surface of said polymeric matrix structure.

9. The method of claim 1, wherein said polymeric matrix structure comprises multiple matrix layers and wherein the first cell population and a second cell population are deposited on separate matrix layers and said matrix layers are attached together to form a laminar structure.

10. The method of claim 1, wherein the biocompatible polymeric matrix structure is formed from a material selected from the group of materials consisting of cellulose ether, cellulose, cellulosic ester, fluorinated polyethylene, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, polyglycolic acid, collagen, poly(alpha esters), poly(lactic acid), polyorthoesters, polyanhydrides, regenerated cellulose, silicone, urea-formaldehyde, copolymers thereof, and physical blends thereof.

11. The method of claim 10, wherein the polymeric matrix structure comprises polyglycolic acid.

12. The method of claim 1, wherein the polymeric matrix structure is comprised of fibers with an interfiber distance between about 0 to 1000 μm.

13. The method of claim 1, wherein the polymeric matrix structure is comprised of fibers with an interfiber distance between about 0 to 500 μm.

14. The method of claim 1, wherein the polymeric matrix structure is comprised of fibers with an interfiber distance between about 0 to 200 μm.

15. The method of claim 1, wherein the first cell population deposited is a population of autologous cells.

16. The method of claim 1, wherein the first cell population is a population of allogeneic cells.

17. The method of claim 1, wherein the polymeric matrix structure is biodegradable.

18. The method of claim 1, wherein upon implantation of said organized matrix/cell construct into a human, said device forms a laminarily organized functional bladder.

* * * * *